United States Patent [19]

Merchant

[11] 3,979,595
[45] Sept. 7, 1976

[54] KNEE SUPPORT AND CASSETTE HOLDER FOR AXIAL X-RAYS OF THE KNEES

[76] Inventor: Alan C. Merchant, 23415 Camino Hermoso, Los Altos Hills, Calif. 94022

[22] Filed: Apr. 9, 1975

[21] Appl. No.: 557,800

[52] U.S. Cl. .............................. 250/451; 250/456
[51] Int. Cl.² ............... G01N 21/00; G01N 23/00; H01J 37/20
[58] Field of Search .................... 250/451, 456, 444

[56] References Cited
UNITED STATES PATENTS

| | | | |
|---|---|---|---|
| 3,452,977 | 7/1969 | Ryman | 250/456 |
| 3,648,305 | 3/1972 | Ersek | 250/456 |

*Primary Examiner*—Alfred E. Smith
*Assistant Examiner*—T. N. Grigsby

[57] ABSTRACT

A frame which holds the legs, knees, and x-ray film cassette in proper alignment to one another would allow an accurate, easily reproducible, and comfortable technique for obtaining an improved axial x-ray view of the kneecaps and patellofemoral joints. (Axial views are those obtained when the x-ray beam is projected in line with the limb, rather than perpendicular to it.)

Heretofore all other techniques to x-ray the knees in axial projection have had significant deficiencies singly or in combination: distortion of the x-ray image, discomfort for the patient with an acutely injured knee, complicated technology applicable to research but not clinical practice, obsolescence due to the larger present-day x-ray tubes and collimators, and improper positioning which masks abnormalities actually present. This frame was developed to allow a technique which avoids these deficiencies. This method has never been described before in the medical literature.

For ease of use it is collapsible, adjustable, and lightweight and can be made from any suitable materials.

5 Claims, 2 Drawing Figures

KNEE SUPPORT AND CASSETTE HOLDER FOR AXIAL X-RAYS OF THE KNEES

BACKGROUND OF THE INVENTION

This invention relates to the field of Radiology and Orthopedic Surgery. It more particularly relates to x-ray film cassette and leg holders and to a new and improved method of obtaining the axial x-ray view of the knee (patellofemoral joint). This invention allows the patient to be placed supine (face up) on the x-ray table with the knees flexed over the end of the table and the legs supported. The knees are elevated slightly with the adjustment provided to keep the femurs (thigh bones) parallel with the table surface. The x-ray tube and collimator can now be raised over the patient for clearance and the x-ray beam projected downward at an angle. The x-ray film cassette is placed in a holder below the knees and rested on the shins perpendicular to the x-ray beam. The legs are strapped together to control rotation, relax the thigh muscles, and to expose both knees simultaneously. Thus an accurate, reproducible, standardized axial x-ray view of the kneecaps (and patellofemoral joints) is obtained which is comfortable even for the recently injured knee.

So far as is known, this simple Knee Support and Cassette Holder for axial x-rays of the knees described and claimed herein has not been known heretofore. A search of previously issued patents reveals none which relates to the problems encountered in obtaining axial x-ray views of the knee. Furthermore, the closest patents granted discovered in said search relate to an x-ray table (U.S. Pat. No. 1,015,187, Kelly, Jan. 16, 1912), two devices to facilitate x-ray views of the skull (U.S. Pat. No. 2,111,903, Rona, Mar. 22, 1938 and U.S. Pat. No. 2,220,725, Moe, Nov. 5, 1940), and a frame for portable chest x-rays (U.S. Pat. No. 3,705,984, Westenberger, Dec. 12, 1972). None is applicable to the instant invention for knee x-rays.

A search of the medical literature reveals several different methods to obtain axial x-ray views of the kneescaps and patellofermoral joints, all with various deficiencies. The most common technique (Settegast) requires no frame or cassette holder but acutely flexes the knee to obtain the exposure. This draws the kneecap (patella) so far into the intercondylar sulcus that a subluxation (partial dislocation) even if present in slight flexion could not be shown with this view. Also in the event of a recently injured knee it is too painful to acutely flex the knee to obtain this view. Therefore, the axial view is omitted and a fracture or loose bone fragment is occasionally missed. The present invention allows comfortable support of the knee in slight flexion which not only reveals any tendency to slight subluxation of the kneecap but also is the position of maximum comfort for the painful knee.

The modified Jaroschy technique also in current use requires no additional frame or holder and does not require acute flexion of the knee. However, the x-ray beam strikes the x-ray film plane at an angle of 45 degrees causing serious distortion of the image, and the rotation of the legs is not controlled introducing another variable. The present invention obviates these difficulties by holding the x-ray cassette perpendicular to the x-ray beam eliminating distortion, and providing a strap for the legs to control rotation yet allow relaxation.

The method of Brattstrom gives accurate films but is so technically elaborate and complex that it is only applicable for research not clinical use. In addition it utilizes a position of acute flexion incurring the problems mentioned above in reference to the Settegast technique.

The methods of Knuttson and Furmaier have been rendered obsolete by the enlargement of x-ray tubes and collimators over the years. The size of current equipment prevents it from being placed low enough over the patient to make the exposure. The invention described herein flexes the knees over the end of the x-ray table supporting the legs and thus allows the x-ray tube and collimator to be raised clear of the patient for the exposure.

SUMMARY OF THE INVENTION

This invention relates generally to an improved method of obtaining axial x-ray views of the knees. More particularly this invention holds the legs, knees, and x-ray film cassette in proper relationship to each other, in a comfortable position, in order to obtain a distortion free axial x-ray image of the kneecaps and patellofemoral joints. Flexion of the knees over the end of the x-ray table allows the x-ray tube and collimator to be lifted over the patient for clearance. The invention supports the knees and legs comfortably and controls rotation. It also holds the x-ray film cassette in a plane perpendicular to the x-ray beam for a distortion free image.

Therefore, from the foregoing it should be understood that objects of this invention include: an improved method of obtaining axial x-ray views of the knees; the provision that the exposure can be made with the knees in a comfortable position of slight flexion; that the angle of flexion can be varied depending on the particular area of the patellofemoral joint to be studied; the provision that rotation of the legs is controlled; the provision for holding the x-ray film cassette perpendicular to the x-ray beam to eliminate distortion; the provision that the x-ray tube can be raised high enough over the patient for adequate clearance; the provision for height adjustment to adapt to different size x-ray tables; the provision for folding for portability and storage; the provision that it can either stand free from or be attached to the x-ray table as desired.

These and other objects of this invention will become apparent from a study of the following disclosure in which reference is directed to the attached drawings.

Figure 1:
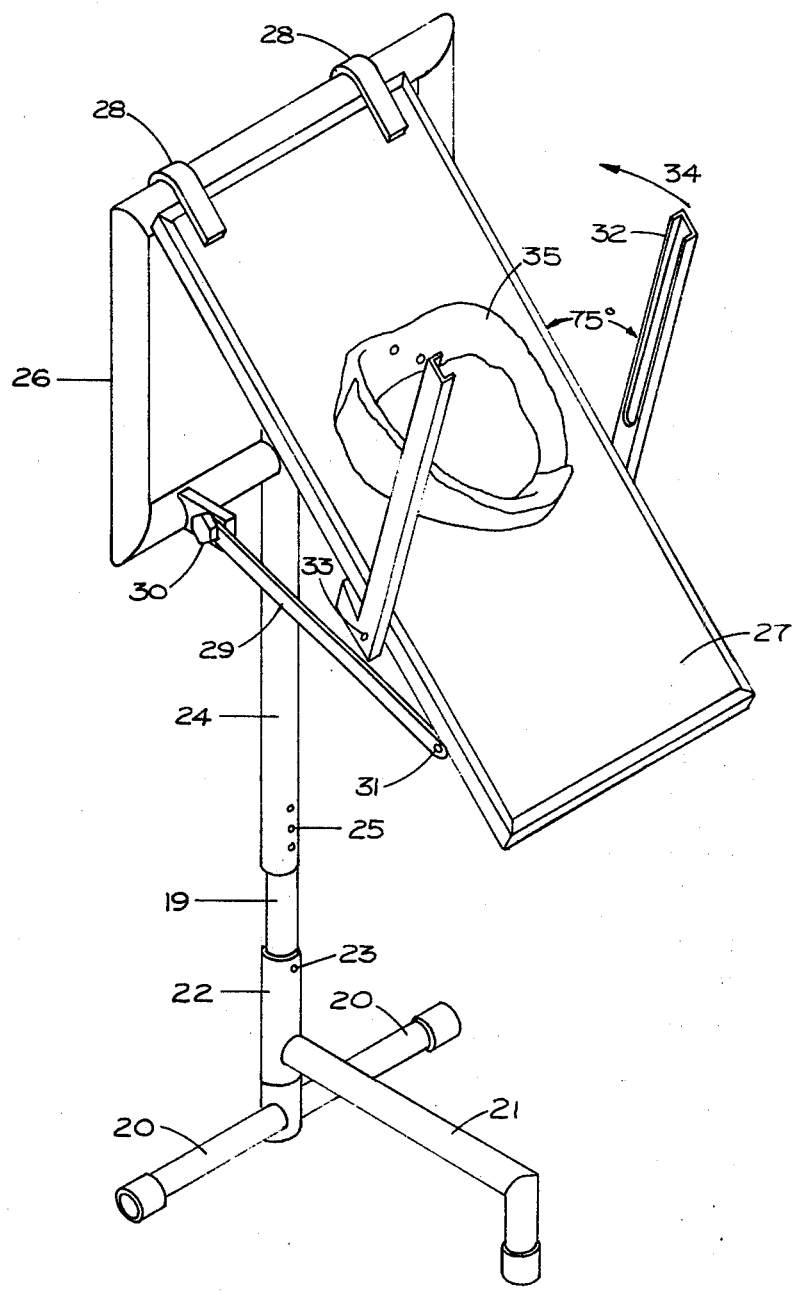
FIG. 1 is a partial perspective view of an exemplary knee support and cassette holder embodying the features of the present invention.

The present invention is subject to various modifications and alternate constructions, but the illustrative details shown in the drawings will be fully described. It should be understood that it is not intended to limit the invention to the particular form shown, but rather the illustration is to cover all modifications, changes, similarities, and alternative methods of construction falling within the spirit and scope of the invention as expressed in the claims below.

DESCRIPTION OF THE PREFERRED EMBODIMENT

Figure 2:
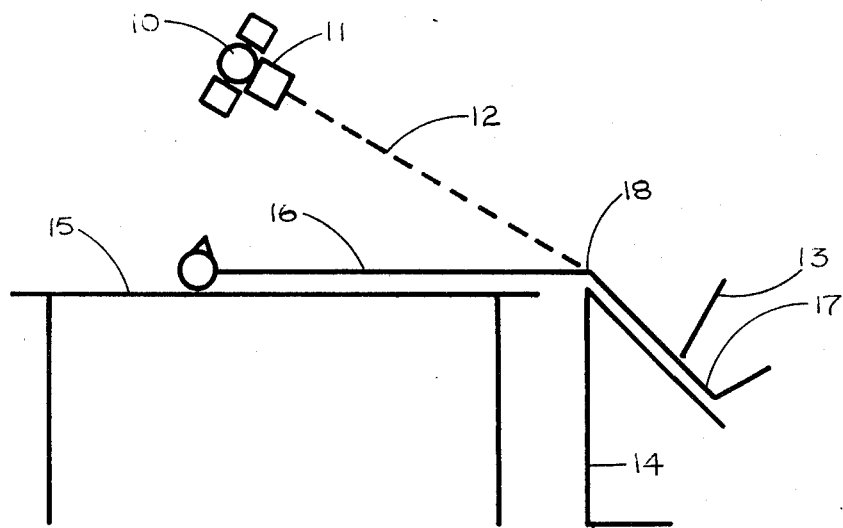
FIG. 2 is a stick figure side view diagram showing the position of the patient, the x-ray tube, its central beam, the x-ray film cassette, and the exemplary device depicted in FIG. 1 in use during an exposure for an axial view of the knees.

Referring now to FIGS. 1 and 2, an exemplary device for holding the knees and legs of a patient and for holding an x-ray film cassette in proper alignment one to another is shown.

Referring now to FIG. 2, the general configuration of a patient positioned on an x-ray table and on the instant invention in the process of taking an axial x-ray view of the knees and patellofemoral joints is shown. The patient 16 is supine (face up) on the x-ray table 15 with his legs and feet 17 supported by the instant invention 14. The x-ray tube 10 and collimator 11 are overhead and angled downward with the central x-ray beam 12 projecting through the patellas (kneecaps) 18 to cast an image on the x-ray film cassette 13 maintained in a position perpendicular to the central x-ray beam 12 by the instant invention 14. Note that nothing projects from the rear of the knee support and x-ray cassette holder 14 so that it can stand flush against the end of the x-ray table 15.

Referring now to FIG. 1, the instant invention is shown. The central support 19 is attached securely to the cross legs 10. The third leg 21 provides a tripod support and is attached to the central support 19 by means of a sleeve 22. This sleeve 22 allows the third leg 21 to be swung laterally for folding and is secured in either position by spring loaded retractable pins which fit into appropriate holes 23.

The upper central support 24 telescopes over the lower central support 19 in order to adjust the height of the entire device. Spring loaded retractable pins fitting in appropriate holes 25 secure the central support at various heights. A square shaped knee support frame 26 is securely attached to the upper central support 24.

A flat leg support 27 is hinged to the knee support 26 by strap hinges 28. The leg support 27 is held in position by struts 29 which are hinged to the knee support frame 26 by hinges 30, and which struts are secured to the leg support 27 at the other end by detachable brackets 31. When the brackets 31 are released, the struts 29 swing downward allowing the leg support 27 to fold flat for storage.

The x-ray film cassette holder is comprised of two upright U-shaped channels 32 with their open sides facing one another and spaced appropriately in order to accept a standard x-ray film cassette by sliding it in from the top. A cross member 33 is rigidly fastened to the two upright channels 32 and provided with a 15° bevel or appropriate stops on its upper surface. The upright channels 32 and the beveled cross member 33 are then hinged to the leg support 27 so that the uprights can fold flat in the direction of the arrow 34 for storage yet upon unfolding for use, the beveled cross member 33 abuts against the flat undersurface of the leg support 27 maintaining the cassette holding channels 32 at the correct 75° angle with the flat leg support 27.

A strap 35 with Velcro, buckle, or other fastening device is affixed in the midline of the flat leg support 27 in order to hold the patient's knees together to control rotation of the limbs yet allow the patient to relax.

What is claimed is:

1. An x-ray film cassette and leg holder comprising:
    A. A knee support frame;
    B. A leg support member hingedly secured to said frame for supporting legs over the end of an x-ray table; and
    C. An x-ray film cassette holder secured to said leg support member for maintaining a cassette in a plane perpendicular to the central x-ray beam aimed down at an angle toward the knee caps.

2. An x-ray film cassette and leg holder as in claim 1 and further including means for adjusting the height of said support frame.

3. An x-ray film cassette and leg holder as in claim 2 and further including means for altering the angle of knee flexion in order to study the knee joints in different attitudes of flexion.

4. An x-ray film cassette and leg holder as in claim 3 and further including means by which it can be folded, collapsed, or easily dismantled for storage or transport.

5. An x-ray film cassette and leg holder as in claim 4 and further including means by which it can be attached to an existing x-ray table by appropriate retention brackets.

* * * * *